United States Patent [19]

Gánshirt et al.

[11] Patent Number: 4,460,365

[45] Date of Patent: Jul. 17, 1984

[54] POLYURETHANE BAG FOR BLOOD

[75] Inventors: Karlheinz Gánshirt, Dreieich; Wolfram H. Walker, Ober-Roden; Hans Schleussner, Frankfurt am Main, all of Fed. Rep. of Germany

[73] Assignee: Biotest-Serum Institute GmbH, Frankfurt am Main, Fed. Rep. of Germany

[21] Appl. No.: 80,622

[22] Filed: Oct. 1, 1979

Related U.S. Application Data

[63] Continuation of Ser. No. 813,368, Jul. 6, 1977, abandoned.

[30] Foreign Application Priority Data

Jul. 8, 1976 [DE] Fed. Rep. of Germany ... 7621615[U]

[51] Int. Cl.³ ........ A61F 1/24

[52] U.S. Cl. ........ 604/408; 128/DIG. 24

[58] Field of Search ........ 128/272, 214 D, DIG. 24; 150/0.5, 1, 8

[56] References Cited

U.S. PATENT DOCUMENTS

| | | | |
|---|---|---|---|
| 3,695,507 | 10/1972 | Sams | 150/1 |
| 3,788,374 | 1/1974 | Saijo | 128/272 |
| 3,940,802 | 3/1976 | Sako et al. | 128/214 D |
| 3,942,529 | 3/1976 | Waage | 128/DIG. 24 |
| 3,946,780 | 3/1976 | Sellers | 150/8 |
| 4,010,783 | 3/1977 | Ralston | 128/214 D |

FOREIGN PATENT DOCUMENTS

| | | | |
|---|---|---|---|
| 2330101 | 9/1975 | Fed. Rep. of Germany | 128/214 D |

*Primary Examiner*—Benjamin R. Padgett
*Assistant Examiner*—Thomas Wallen
*Attorney, Agent, or Firm*—Sprung, Horn, Kramer & Woods

[57] ABSTRACT

A bag suitable for the storage, deep-freezing and transfusion of blood and blood components formed of a calendered or extruded foil of plasticizer-free polyurethane of a thickness of about 0.1–0.5 mm, a Shore hardness A of about 60–85, temperature resistance up to about 160° C. and down to about −196° C. without change of properties. The bag can be used in combination with fittings and tubings of the same material to provide an overall plasticizer-free polyurethane system. The bag can be sterilized, is capable of low temperature storage, and exhibits other desirable properties without affecting the quality of its contents.

4 Claims, 1 Drawing Figure

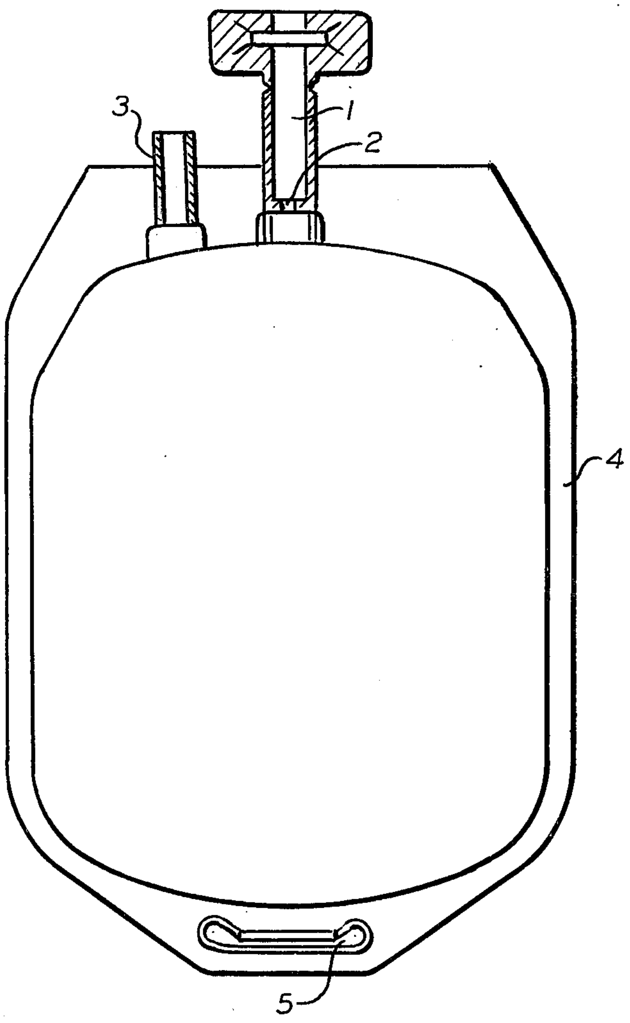
3
1
2
4
5

POLYURETHANE BAG FOR BLOOD

This is a continuation of application Ser. No. 813,368, filed July 6, 1977 now abandoned.

The invention relates to blood-, plasma-, transfusion- and infusion bags as well as to bag systems used as recipients and for storage, conservation, deep-freezing and transfusion of blood, plasma and cellular blood components, and these bags are at the same time filled with or without anticoagulant solution for fluid storage and are used with or without addition of protective solutions without requiring any transfer of solutions of bags to special protective containers.

In general, the following requirements are made of bags used for these purposes: They must be transparent and flexible, they must be steam-sterilizable when filled with aqueous blood anticoagulant liquid or they must be sterilizable with ethylene oxide or radiation when empty. In addition, the plastic material of which such bags are customarily made must be compatible with blood, must not give off any substances harmful to the blood or the patient, must not eliminate any substances from the blood, must not influence the clotting system of the blood, must not have any harmful influence on the plasmatic and cellular ingredients of the blood such as erythrocytes, thrombocytes and leucocytes and it must be impervious to invasion of microorganisms.

Bags for the above mentioned purposes have hitherto been made mostly from plasticizer-containing polyvinyl chloride. Polyvinyl chloride has good features such as transparency and easy workability. In addition, it is available in various grades of stiffness. It is flexible to solid, depending on its plasticizer content, and hence can be utilized for various purposes.

The plasticized polyvinyl chloride, which also contains stabilizers and lubricants, has the disadvantage that when storing blood and plasma in these bags, considerable amounts of these additions, e.g. the plasticizer and/or the stabilizer, can be leached out. In addition, extruded or calendered and transparent polyvinyl chloride has a tendency to make the flat bags stick together during steam sterilization. For this reason, roughened foil surfaces are frequently used which, however, do not have very good blood-compatible qualities.

Calendered or extruded soft foils, moreover, shrink up to 20% during thermal treatment, e.g. sterilization with saturated water vapor, depending on the thickness, flexibility and surface. Since these shrinkages depend on orientation and since they vary, this too creates difficulties for a homogeneous production of the bags.

For long-term conservation of blood and blood components, the biologic material is deep frozen with or without addition of protective solutions at −25° to −80° C. or −196° C. Bags made of polyvinyl chloride are only conditionally suitable therefore, as they are extremely brittle already at −25° C. and tend to crack. This is the reason why special containers made of aluminum, polyolefin or polytetrafluoroethylene are used for instance for deep freezing of erythrocytes at −80° C. or at liquid nitrogen temperatures. Since blood and blood components are normally stored in fluid state in glass bottles or in known blood bags made of plasticized polyvinyl chloride, a refilling into these special containers is necessary for deep freezing. Aside from the extra labor and the costs for the two-bag-system, there is the danger of bacterial contamination of the content.

It was discovered that the above described disadvantages and difficulties are overcome when using foils of polyurethane as bag material.

Specifically, the invention provides bags used as receipients and for storage, deep-freezing and transfusion of blood and blood components formed from a polyurethane foil of about 0.1–0.5 mm thickness, Shore hardness A of about 60–85, temperature resistance up to about 160° C. and down to about −196° C. without change of properties.

Such a foil has good age resistance, low oxygen sensitivity and high hydrolysis resistance.

Polyurethane foils with various properties as well as their production are already known. Polyurethane, as is known, is the poly addition product of di- or poly-isocyanates with di- or poly-hydroxy compounds. These polyols can have a polyester or polyether as basic unit. The foils which are suitable for the new bags must be flexible, transparent, sterilizable, weldable and/or sealable to one another with solvents or with plasticized polyvinyl chloride. In contrast to plasticized polyvinyl chloride, polyurethane foils with these special criteria show, due to low moisture absorption, only minor, if any, turbidity. Since such polyurethane foils contain neither stabilizers nor lubricants nor plasticizers nor polymerization initiators, they are particularly suitable for the storage of blood and blood components. Tests have shown that aqueous autoclaving of this special foil complies for instance with the chemical requirements DIN 58 368 Draft 1965 and DIN 58 361 Draft 1977 for systems for the storage and transfusion of blood and blood components.

Since such polyurethanes are suitable also for the production of injection molded parts and for the extrusion of tubings, an entire bag system for blood and blood components comprising fittings, tubing and satellite bags can consist of one and the same material. The bags are also suitable for the preparation, storage and application of infusion solutions.

Another advantage of the new bags made of the special material is, among others, that these polyurethane foils show favorable shrinkage properties during steam sterilization. For instance, a 0.4 mm thick extruded foil has a shrinkage value in the direction of extrusion of less than 2% and an elongation of less than 1%. The selected polyurethane material also shows particularly favorable deep-freezing properties and tends neither to become brittle at low temperatures nor to form cracks. These new bags are therefore suitable as recipient and for storage of blood and blood components, as well as for deep freezing of blood cells and plasma and its derivatives. The simultaneous applicability as fluid storage container and as deep-freeze container eliminates the cumbersome and risky refilling of the blood components into special containers.

A bag made of the new material can, for instance, be constructed as the commonly marketed plastic bags for blood, blood components and infusion solutions.

This drawing shows a bag for blood and blood components which has a connecting part 1 for a puncture plug (not shown), a membrane 2 and connecting part 3 for an intake and discharge tube. The rim 4 of the bag has an integral hanger device 5.

It will be appreciated that the instance specification and examples are set forth by way of illustration and not limitation, and that various modifications and changes may be made without departing from the spirit and scope of the present invention.

What is claimed is:

1. A bag suitable for the storage, deep-freezing and transfusion of blood and blood components and infusion solutions formed of a calendered or extruded foil of plasticizer free polyurethane of a thickness of about 0.1–0.5 mm, a Shore hardness A of about 60–85, temperature resistance up to about 160° C. and down to about −196° C. without change of properties.

2. A blood-receiving-and-dispensing-system comprising a bag according to claim 1 in combination with injection-molded fittings and tubings communicating with the bag and satellite bags said fittings and tubings comprising plasticizer-free polyurethane.

3. A bag according to claim 1 containing blood or a blood component.

4. In the conservation of blood or a blood component wherein blood or a blood component is placed in a container, stored at a temperature below −25° C., brought back to room temperature and administered, the improvement which comprises employing as the container a bag according to claim 1, whereby the same container can be sterilized and stored as the cold-temperature storage container.

* * * * *